United States Patent
Swanson

(10) Patent No.: US 8,016,822 B2
(45) Date of Patent: *Sep. 13, 2011

(54) FLUID INJECTING DEVICES AND METHODS AND APPARATUS FOR MAINTAINING CONTACT BETWEEN FLUID INJECTING DEVICES AND TISSUE

(75) Inventor: David K. Swanson, Campbell, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1178 days.

This patent is subject to a terminal disclaimer.

(21) Appl. No.: 11/141,405

(22) Filed: May 28, 2005

(65) Prior Publication Data

US 2006/0271034 A1    Nov. 30, 2006

(51) Int. Cl.
*A61B 18/12* (2006.01)
(52) U.S. Cl. .................. 606/41; 606/1; 606/40; 606/42; 606/51
(58) Field of Classification Search .................. 606/1–52
See application file for complete search history.

(56) References Cited

U.S. PATENT DOCUMENTS

| | | |
|---|---|---|
| 3,805,793 A | 4/1974 | Wright |
| 3,998,215 A | 12/1976 | Anderson et al. |
| 4,326,529 A | 4/1982 | Doss |
| 4,469,105 A | 9/1984 | Staver |
| 4,646,747 A | 3/1987 | Lundback |
| 4,682,596 A | 7/1987 | Bales |
| 4,685,466 A | 8/1987 | Rau |
| 4,736,749 A | 4/1988 | Lundback |
| 4,832,048 A | 5/1989 | Cohen |
| 4,919,648 A | 4/1990 | Sibalis |
| 5,055,100 A | 10/1991 | Olsen |
| 5,085,657 A | 2/1992 | Ben-Simhon |
| 5,224,944 A | 7/1993 | Elliott |
| 5,281,213 A | 1/1994 | Milder |
| 5,292,320 A | 3/1994 | Brown |

(Continued)

FOREIGN PATENT DOCUMENTS

EP    0856292 A1    8/1998

(Continued)

OTHER PUBLICATIONS

Office Action dated Dec. 7, 2004 for U.S. Appl. No. 10/395,021, filed Mar. 21, 2003, Inventor: David K. Swanson (7 pages).

(Continued)

*Primary Examiner* — Sam Yao
*Assistant Examiner* — Aaron Roane
(74) *Attorney, Agent, or Firm* — Vista IP Law Group LLP

(57) ABSTRACT

Apparatus and methods for maintaining contact between tissue and a fluid injection device. An apparatus in the form of a suction device for use with a probe that includes at least one energy transmission device and a wettable structure around at least a portion of the energy transmission device includes a suction pod and a connector. The suction pod defines a suction region and includes a suction aperture within the suction region. The connector is configured to secure the probe to the suction device such that at least a portion of the wettable structure is within the suction region in spaced relation to the suction aperture. A support device positioned within the suction region is configured to engage the wettable structure and maintain a predetermined space between the wettable structure and the suction aperture.

19 Claims, 7 Drawing Sheets

U.S. PATENT DOCUMENTS

| | | |
|---|---|---|
| 5,295,481 A | 3/1994 | Geeham |
| 5,318,262 A | 6/1994 | Adams |
| 5,330,518 A | 7/1994 | Neilson |
| 5,334,193 A | 8/1994 | Nardella |
| 5,336,170 A | 8/1994 | Salerno |
| 5,348,554 A | 9/1994 | Imran |
| 5,383,876 A | 1/1995 | Nardella |
| 5,398,683 A | 3/1995 | Edwards |
| 5,409,483 A | 4/1995 | Campbell |
| 5,443,470 A | 8/1995 | Stern |
| 5,450,846 A | 9/1995 | Goldreyer |
| 5,496,271 A | 3/1996 | Burton |
| 5,505,730 A | 4/1996 | Edwards |
| 5,545,193 A | 8/1996 | Fleischman |
| 5,569,241 A | 10/1996 | Edwards |
| 5,569,242 A | 10/1996 | Lax |
| 5,571,088 A | 11/1996 | Lennox et al. |
| 5,575,772 A | 11/1996 | Lennox |
| 5,582,609 A | 12/1996 | Swanson |
| 5,584,872 A | 12/1996 | LaFontaine |
| 5,609,151 A | 3/1997 | Mulier |
| 5,613,659 A | 3/1997 | Hong |
| 5,624,392 A | 4/1997 | Saab |
| 5,630,837 A | 5/1997 | Crowley |
| 5,637,090 A | 6/1997 | McGee |
| 5,637,884 A | 6/1997 | Yang |
| 5,673,695 A | 10/1997 | McGee |
| 5,676,693 A | 10/1997 | LaFontaine |
| 5,683,366 A | 11/1997 | Eggers |
| 5,688,267 A | 11/1997 | Panescu |
| 5,697,536 A | 12/1997 | Eggers |
| 5,697,882 A | 12/1997 | Eggers |
| 5,697,927 A | 12/1997 | Imran |
| 5,755,715 A | 5/1998 | Stern |
| 5,782,899 A | 7/1998 | Imran |
| 5,785,706 A | 7/1998 | Bednarek |
| 5,792,140 A | 8/1998 | Tu |
| 5,797,903 A | 8/1998 | Swanson |
| 5,797,905 A | 8/1998 | Fleischman |
| 5,800,482 A | 9/1998 | Pomeranz |
| 5,800,484 A | 9/1998 | Gough |
| 5,807,395 A | 9/1998 | Mulier |
| 5,824,005 A | 10/1998 | Motamedi |
| 5,833,690 A | 11/1998 | Yates |
| 5,840,076 A | 11/1998 | Swanson et al. |
| 5,861,021 A | 1/1999 | Thome |
| 5,879,348 A | 3/1999 | Owens |
| 5,891,134 A | 4/1999 | Goble |
| 5,910,129 A | 6/1999 | Koblish |
| 5,913,854 A | 6/1999 | Maguire |
| 5,938,659 A | 8/1999 | Tu |
| 5,938,694 A | 8/1999 | Jaraczewski |
| 5,951,546 A | 9/1999 | Lorentzen |
| 5,957,922 A | 9/1999 | Imran |
| 5,961,513 A | 10/1999 | Swanson |
| 5,971,983 A | 10/1999 | Lesh |
| 6,002,968 A | 12/1999 | Edwards |
| 6,004,269 A | 12/1999 | Crowley et al. |
| 6,012,457 A | 1/2000 | Lesh |
| 6,015,407 A | 1/2000 | Rieb |
| 6,017,338 A | 1/2000 | Brucker |
| 6,023,638 A | 2/2000 | Swanson |
| 6,024,740 A | 2/2000 | Lesh |
| 6,032,077 A | 2/2000 | Pomeranz |
| 6,032,672 A | 3/2000 | Taylor |
| 6,036,697 A | 3/2000 | DiCaprio |
| 6,048,329 A | 4/2000 | Thompson |
| 6,053,912 A | 4/2000 | Panescu |
| 6,053,937 A | 4/2000 | Edwards |
| 6,068,653 A | 5/2000 | LaFontaine |
| 6,071,274 A | 6/2000 | Thompson |
| 6,071,279 A | 6/2000 | Whayne |
| 6,071,281 A | 6/2000 | Burnside |
| 6,076,012 A | 6/2000 | Swanson |
| 6,115,626 A | 9/2000 | Whayne et al. |
| 6,117,101 A | 9/2000 | Diederich |
| 6,142,994 A | 11/2000 | Swanson et al. |
| 6,159,207 A | 12/2000 | Yoon |
| 6,164,283 A | 12/2000 | Lesh |
| 6,168,594 B1 | 1/2001 | LaFontaine |
| 6,185,442 B1 | 2/2001 | Samson |
| 6,190,381 B1 | 2/2001 | Olsen et al. |
| 6,237,605 B1 | 5/2001 | Vaska et al. |
| 6,241,727 B1 | 6/2001 | Tu |
| 6,258,087 B1 | 7/2001 | Edwards |
| 6,264,654 B1 | 7/2001 | Swartz |
| 6,270,493 B1 | 8/2001 | Lalonde |
| 6,277,115 B1 | 8/2001 | Saadat |
| 6,280,441 B1 | 8/2001 | Ryan |
| 6,287,301 B1 | 9/2001 | Thompson |
| 6,290,699 B1 | 9/2001 | Hall |
| 6,306,133 B1 | 10/2001 | Tu |
| 6,308,104 B1 | 10/2001 | Taylor |
| 6,311,692 B1 | 11/2001 | Vaska et al. |
| 6,314,962 B1 | 11/2001 | Vaska et al. |
| 6,325,797 B1 | 12/2001 | Stewart |
| 6,364,876 B1 | 4/2002 | Erb et al. |
| 6,371,955 B1 | 4/2002 | Fuimaono |
| 6,394,948 B1 | 5/2002 | Borst et al. |
| 6,447,443 B1 | 9/2002 | Keogh et al. |
| 6,464,700 B1 | 10/2002 | Koblish et al. |
| 6,468,272 B1 | 10/2002 | Koblish |
| 6,475,179 B1 | 11/2002 | Wang |
| 6,485,489 B2 | 11/2002 | Teirstein |
| 6,488,680 B1 | 12/2002 | Francischelli et al. |
| 6,511,416 B1 * | 1/2003 | Green et al. ............... 600/37 |
| 6,514,250 B1 * | 2/2003 | Jahns et al. ............... 606/41 |
| 6,522,905 B2 | 2/2003 | Desai |
| 6,522,930 B1 | 2/2003 | Schaer et al. |
| 6,527,767 B2 | 3/2003 | Wang et al. |
| 6,529,756 B1 | 3/2003 | Phan et al. |
| 6,542,781 B1 | 4/2003 | Koblish et al. |
| 6,558,382 B2 | 5/2003 | Jahns et al. |
| 6,575,969 B1 | 6/2003 | Rittman, III et al. |
| 6,579,288 B1 | 6/2003 | Swanson |
| 6,584,360 B2 | 6/2003 | Francischelli et al. |
| 6,645,202 B1 | 11/2003 | Pless et al. |
| 6,652,518 B2 | 11/2003 | Wellman et al. |
| 6,663,622 B1 | 12/2003 | Foley et al. |
| 6,676,597 B2 | 1/2004 | Guenst et al. |
| 6,692,491 B1 | 2/2004 | Phan |
| 6,706,038 B2 | 3/2004 | Francischelli et al. |
| 6,771,996 B2 | 8/2004 | Bowe |
| 6,780,180 B1 | 8/2004 | Goble et al. |
| 6,786,898 B2 | 9/2004 | Guenst |
| 6,814,731 B2 | 11/2004 | Swanson |
| 6,837,885 B2 | 1/2005 | Koblish |
| 6,849,075 B2 | 2/2005 | Bertolero et al. |
| 6,887,238 B2 | 5/2005 | Jahns et al. |
| 6,893,442 B2 | 5/2005 | Whayne |
| 6,926,712 B2 | 8/2005 | Phan |
| 6,939,350 B2 | 9/2005 | Phan |
| 6,942,661 B2 | 9/2005 | Swanson |
| 7,020,531 B1 | 3/2006 | Colliou et al. |
| 7,077,842 B1 | 7/2006 | Cosman |
| 7,149,575 B2 | 12/2006 | Ostroff et al. |
| 7,250,048 B2 | 7/2007 | Francischelli et al. |
| 7,326,206 B2 | 2/2008 | Paul et al. |
| 7,371,233 B2 * | 5/2008 | Swanson et al. ............... 606/41 |
| 2001/0007071 A1 | 7/2001 | Koblish |
| 2002/0002372 A1 | 1/2002 | Jahns et al. |
| 2002/0026187 A1 | 2/2002 | Swanson |
| 2002/0095067 A1 | 7/2002 | Guenst et al. |
| 2003/0014049 A1 | 1/2003 | Koblish et al. |
| 2003/0036754 A1 | 2/2003 | Erb |
| 2003/0060685 A1 | 3/2003 | Houser |
| 2003/0069570 A1 | 4/2003 | Witzel |
| 2003/0069572 A1 * | 4/2003 | Wellman et al. ............... 606/41 |
| 2003/0078575 A1 | 4/2003 | Jahns et al. |
| 2003/0078644 A1 | 4/2003 | Phan |
| 2003/0083655 A1 | 5/2003 | Van Wyk |
| 2003/0120268 A1 | 6/2003 | Bertolero et al. |
| 2003/0139644 A1 * | 7/2003 | Parsons et al. ............... 600/37 |
| 2003/0153905 A1 | 8/2003 | Edwards et al. |
| 2003/0158547 A1 | 8/2003 | Phan |
| 2003/0167056 A1 | 9/2003 | Jahns et al. |
| 2003/0216724 A1 | 11/2003 | Jahns |

| | | | |
|---|---|---|---|
| 2004/0006336 | A1 | 1/2004 | Swanson |
| 2004/0138522 | A1 | 7/2004 | Haarstad |
| 2004/0186467 | A1 | 9/2004 | Swanson |
| 2004/0267192 | A1 | 12/2004 | Weldon et al. |
| 2005/0019545 | A1 | 1/2005 | Riebel |
| 2005/0019653 | A1 | 1/2005 | Dahlberg |
| 2005/0049583 | A1 | 3/2005 | Swanson |
| 2005/0059962 | A1 | 3/2005 | Phan et al. |
| 2005/0119648 | A1 | 6/2005 | Swanson |
| 2005/0119649 | A1 | 6/2005 | Swanson |
| 2005/0119654 | A1 | 6/2005 | Swanson |
| 2005/0222564 | A1 | 10/2005 | Plaza |
| 2005/0261673 | A1 | 11/2005 | Bonner et al. |
| 2006/0047277 | A1 | 3/2006 | Eberl et al. |
| 2006/0155274 | A1 | 7/2006 | Swanson et al. |
| 2007/0198041 | A1* | 8/2007 | Rupp et al. .................... 606/184 |

FOREIGN PATENT DOCUMENTS

| | | |
|---|---|---|
| EP | 1125549 A2 | 8/2001 |
| EP | 1169972 A1 | 1/2002 |
| WO | WO-97/10753 A1 | 3/1997 |
| WO | WO 99/48421 A1 | 9/1999 |
| WO | WO 00/56237 A1 | 9/2000 |
| WO | WO-01/58373 A1 | 8/2001 |
| WO | WO 02/17804 A1 | 3/2002 |
| WO | WO 03/024305 A2 | 3/2003 |
| WO | WO 2004/093698 A1 | 11/2004 |

OTHER PUBLICATIONS

Amendment dated Apr. 6, 2005 for U.S. Appl. No. 10/395,021, filed Mar. 21, 2003, Inventor: David K. Swanson (17 pages).
Office Action date May 17, 2005 for U.S. Appl. No. 10/395,021, filed Mar. 21, 2003, Inventor: David K. Swanson (9 pages).
Amendment dated Oct. 17, 2005 for U.S. Appl. No. 10/395,021, filed Mar. 21, 2003, Inventor: David K. Swanson (12 pages).
Office Action dated Nov. 28, 2005 for U.S. Appl. No. 10/395,021, filed Mar. 21, 2003, Inventor: David K. Swanson (7 pages).
Amendment dated Jan. 30, 2006 for U.S. Appl. No. 10/395,021, filed Mar. 21, 2003, Inventor: David K. Swanson (12 pages).
Office Action dated Apr. 10, 2006 for U.S. Appl. No. 10/395,021, filed Mar. 21, 2003, Inventor: David K. Swanson (5 pages).
Amendment dated Apr. 12, 2006 for U.S. Appl. No. 10/395,021, filed Mar. 21, 2003, Inventor: David K. Swanson (10 pages).
Office Action dated May 10, 2006 for U.S. Appl. No. 10/395,021, filed Mar. 21, 2003, Inventor: David K. Swanson (6 pages).
Amendment dated Aug. 15, 2006 for U.S. Appl. No. 10/395,021, filed Mar. 21, 2003, Inventor: David K. Swanson (14 pages).
Office Action dated Oct. 24, 2006 for U.S. Appl. No. 10/395,021, filed Mar. 21, 2003, Inventor: David K. Swanson (7 pages).
Amendment and Request for Continued Examination dated Jan. 23, 2007 for U.S. Appl. No. 10/395,021, filed Mar. 21, 2003, Inventor: David K. Swanson (24 pages).
Office Action dated Mar. 27, 2007 for U.S. Appl. No. 10/395,021, filed Mar. 21, 2003, Inventor: David K. Swanson (9 pages).
Amendment dated Jun. 27, 2007 for U.S. Appl. No. 10/395,021, filed Mar. 21, 2003, Inventor: David K. Swanson (18 pages).
Office Action dated Aug. 14, 2007 for U.S. Appl. No. 10/395,021, filed Mar. 21, 2003, Inventor: David K. Swanson (10 pages).
Amendment and Request for Continued Examination dated Oct. 26, 2007 for U.S. Appl. No. 10/395,021, filed Mar. 21, 2003, Inventor: David K. Swanson (21 pages).
Office Action dated Dec. 7, 2007 for U.S. Appl. No. 10/395,021, filed Mar. 21, 2003, Inventor: David K. Swanson (8 pages).
Amendment dated Mar. 28, 2008 for U.S. Appl. No. 10/395,021, filed Mar. 21, 2003, Inventor: David K. Swanson (20 pages).
Office Action dated Jan. 13, 2006 for U.S. Appl. No. 10/727,149, filed Dec. 2, 2003, Inventor: David K. Swanson (20 pages).
Amendment dated Apr. 12, 2006 for U.S. Appl. No. 10/727,149, filed Dec. 2, 2003, Inventor: David K. Swanson (14 pages).
Office Action dated Jun. 30, 2006 for U.S. Appl. No. 10/727,149, filed Dec. 2, 2003, Inventor: David K. Swanson (5 pages).
Response dated Jul. 11, 2006 for U.S. Appl. No. 10/727,149, filed Dec. 2, 2003, Inventor: David K. Swanson (2 pages).
Office Action dated Sep. 15, 2006 for U.S. Appl. No. 10/727,149, filed Dec. 2, 2003, Inventor: David K. Swanson (7 pages).
Amendment dated Dec. 7, 2006 for U.S. Appl. No. 10/727,149, filed Dec. 2, 2003, Inventor: David K. Swanson (14 pages).
Office Action dated Jan. 9, 2007 for U.S. Appl. No. 10/727,149, filed Dec. 2, 2003, Inventor: David K. Swanson (8 pages).
Amendment and Request for Continued Examination dated Apr. 6, 2007 for U.S. Appl. No. 10/727,149, filed Dec. 2, 2003, Inventor: David K. Swanson (15 pages).
Office Action dated Jun. 14, 2007 for U.S. Appl. No. 10/727,149, filed Dec. 2, 2003, Inventor: David K. Swanson (7 pages).
Amendment dated Oct. 15, 2007 for U.S. Appl. No. 10/727,149, filed Dec. 2, 2003, Inventor: David K. Swanson (11 pages).
Office Action dated Dec. 27, 2007 for U.S. Appl. No. 10/727,149, filed Dec. 2, 2003, Inventor: David K. Swanson (6 pages).
Response dated Mar. 11, 2008 for U.S. Appl. No. 10/727,149, filed Dec. 2, 2003, Inventor: David K. Swanson (12 pages).
Office Action dated Apr. 29, 2005 for U.S. Appl. No. 10/727,096, filed Dec. 2, 2003, Inventor: David K. Swanson (6 pages).
Response dated Jun. 14, 2005 for U.S. Appl. No. 10/727,096, filed Dec. 2, 2003, Inventor: David K. Swanson (3 pages).
Office Action dated Aug. 8, 2005 for U.S. Appl. No. 10/727,096, filed Dec. 2, 2003, Inventor: David K. Swanson (12 pages).
Amendment dated Dec. 3, 2005 for U.S. Appl. No. 10/727,096, filed Dec. 2, 2003, Inventor: David K. Swanson (10 pages).
Office Action dated Mar. 7, 2006 for U.S. Appl. No. 10/727,096, filed Dec. 2, 2003, Inventor: David K. Swanson (10 pages).
Amendment and Request for Continued Examination dated May 4, 2006 for U.S. Appl. No. 10/727,096, filed Dec. 2, 2003, Inventor: David K. Swanson (14 pages).
Advisory Action dated May 24, 2006 for U.S. Appl. No. 10/727,096, filed Dec. 2, 2003, Inventor: David K. Swanson (3 pages).
Office Action dated Jul. 13, 2006 for U.S. Appl. No. 10/727,096, filed Dec. 2, 2003, Inventor: David K. Swanson (12 pages).
Amendment dated Nov. 9, 2006 for U.S. Appl. No. 10/727,096, filed Dec. 2, 2003, Inventor: David K. Swanson (14 pages).
Office Action dated Feb. 7, 2007 for U.S. Appl. No. 10/727,096, filed Dec. 2, 2003, Inventor: David K. Swanson (8 pages).
Amendment dated Apr. 27, 2007 for U.S. Appl. No. 10/727,096, filed Dec. 2, 2003, Inventor: David K. Swanson (12 pages).
Office Action dated May 18, 2007 for U.S. Appl. No. 10/727,096, filed Dec. 2, 2003, Inventor: David K. Swanson (8 pages).
Amendment dated Aug. 20, 2007 for U.S. Appl. No. 10/727,096, filed Dec. 2, 2003, Inventor: David K. Swanson (14 pages).
Office Action dated Nov. 9, 2007 for U.S. Appl. No. 10/727,096, filed Dec. 2, 2003, Inventor: David K. Swanson (14 pages).
Amendment and Request for Continued Examination dated Feb. 11, 2008 for U.S. Appl. No. 10/727,096, filed Dec. 2, 2003, David K. Swanson (23 pages).
Office Action dated Mar. 27, 2007 for U.S. Appl. No. 11/067,391, filed Feb. 25, 2005, Inventor: Greg Eberl (5 pages).
Response dated Apr. 16, 2007 for U.S. Appl. No. 11/067,391, filed Feb. 25, 2005, Inventor: Greg Eberl (7 pages).
Office Action dated Jun. 28, 2007 for U.S. Appl. No. 11/067,391, filed Feb. 25, 2005, Inventor: Greg Eberl (12 pages).
Amendment dated Sep. 28, 2007 for U.S. Appl. No. 11/067,391, filed Feb. 25, 2005, Inventor: Greg Eberl (10 pages).
Office Action dated Dec. 28, 2007 for U.S. Appl. No. 11/067,391, filed Feb. 25, 2005, Inventor: Greg Eberl (9 pages).
Amendment dated Mar. 27, 2008 for U.S. Appl. No. 11/067,391, filed Feb. 25, 2005, Inventor: Greg Eberl (11 pages).
Office Action dated Mar. 25, 2008 for U.S. Appl. No. 11/036,631, filed Jan. 8, 2005, Inventor: David K. Swanson (6 pages).
Office Action dated Mar. 24, 2008 for U.S. Appl. No. 11/031,630, filed Jan. 8, 2005, Inventor: David K. Swanson (13 pages).
Office Action dated Jun. 30, 2006 for U.S. Appl. No. 10/784,316, filed Feb. 19, 2004, Inventor: David K. Swanson (5 pages).
Response dated Jul. 13, 2006 for U.S. Appl. No. 10/784,316, filed Feb. 19, 2004, Inventor: David K. Swanson (2 pages).
Office Action dated Sep. 22, 2006 for U.S. Appl. No. 10/784,316, filed Feb. 19, 2004, Inventor: David K. Swanson (13 pages).
Amendment dated Jan. 22, 2007 for U.S. Appl. No. 10/784,316, filed Feb. 19, 2004, Inventor: David K. Swanson (18 pages).

Office Action dated Jul. 10, 2007 for U.S. Appl. No. 10/784,316, filed Feb. 19, 2004, Inventor: David K. Swanson (8 pages).
Amendment dated Oct. 10, 2007 for U.S. Appl. No. 10/784,316, filed Feb. 19, 2004, Inventor: David K. Swanson (16 pages).
Office Action dated Nov. 13, 2007 for U.S. Appl. No. 10/784,316, filed Feb. 19, 2004, Inventor: David K. Swanson (12 pages).
Amendment dated Dec. 21, 2007 for U.S. Appl. No. 10/784,316, filed Feb. 19, 2004, Inventor: David K. Swanson (10 pages).
Terminal Disclaimer dated Dec. 21, 2007 for U.S. Appl. No. 10/784,316, filed Feb. 19, 2004, Inventor: David K. Swanson (3 pages).
Notice of Allowance dated Jan. 15, 2008 for U.S. Appl. No. 10/784,316, filed Feb. 19, 2004, Inventor: David K. Swanson (6 pages).
PCT International Search Report for PCT/US2004/005883, Applicant: Scimed Life Systems, Inc., Forms PCT/ISA/210 and PCT/ISA/220, dated Aug. 2, 2004 (10 pages).
PCT Written Opinion for PCT/US2004/005883, Applicant: Scimed Life Systems, Inc., Form PCT/ISA/237, dated Aug. 2, 2004 (8 pages).
PCT International Preliminary Report on Patentability for PCT/US2004/005883, Applicant: Scimed Life Systems, Inc., Form PCT/IB/326, dated Aug. 2, 2004 (10 pages).
Communication Pursuant to Article 96(2) EPC for EP Application No. 04715649.2, Applicant: Boston Scientific Limited, dated Mar. 22, 2006 (3 pages).
Communication Pursuant to Rule 51(4) EPC for EP Application No. 04715649.2, Applicant: Boston Scientific Limited, dated Dec. 22, 2006 (5 pages).
PCT International Search Report for PCT/US2004/039284, Applicant: Scimed Life Systems, Inc., Form PCT/ISA/210, dated May 11, 2005 (3 pages).
PCT Written Opinion for PCT/US2004/039284, Applicant: Scimed Life Systems, Inc., Form PCT/ISA/237, dated May 11, 2005 (4 pages).
PCT International Preliminary Report on Patentability for PCT/US2004/039284, Applicant: Scimed Life Systems, Inc., Form PCT/IB/373, dated Jun. 7, 2006 (5 pages).
PCT International Search Report for PCT/US2004/039283, Applicant: Scimed Life Systems, Inc., Form PCT/ISA/210, dated Apr. 14, 2005 (3 pages).
PCT Written Opinion for PCT/US2004/039283, Applicant: Scimed Life Systems, Inc., Form PCT/ISA/237, dated Apr. 14, 2005 (7 pages).
PCT International Preliminary Report on Patentability for PCT/US2004/039283, Applicant: Scimed Life Systems, Inc., Form PCT/IB/373, dated Jun. 7, 2006 (8 pages).
PCT International Preliminary Report on Patentability for PCT/US2004/039143, Applicant: Scimed Life Systems, Inc., Form PCT/IB/373, dated Aug. 22, 2006 (6 pages).
PCT International Search Report for PCT/US2004/039143, Applicant: Scimed Life Systems, Inc., Form PCT/ISA/210 (3 pages).
PCT Written Opinion for PCT/US2004/039143, Applicant: Scimed Life Systems, Inc., Form PCT/ISA/237 (5 pages).
Amendment dated Jun. 20, 2008 for related U.S. Appl. No. 11/031,631, filed Jan. 8, 2005, Inventor: David Swanson (19 pages).
Amendment dated Jun. 20, 2008 for related U.S. Appl. No. 11/031,630, filed Jan. 8, 2005, Inventor: David Swanson (10 pages).
Office Action dated Mar. 26, 2008 for related U.S. Appl. No. 11/031,629, filed Jan. 8, 2005, Inventor: David K. Swanson (16 pages).
Office Action dated Apr. 25, 2008 for related U.S. Appl. No. 10/727,096, filed Dec. 2, 2003, Inventor: David Swanson (12 pages).
Jun. 17, 2008 Final Office Action in U.S. Appl. No. 10/395,021.
Applicant, Aug. 18, 2008 Amendment in U.S. Appl. No. 10/727,149.
Applicant, Jul. 24, 2008 Amendment in U.S. Appl. No. 10/727,096.
Sep. 16, 2008 Non-Final Office Action in U.S. Appl. No. 11/031,631.
Sep. 17, 2008 Non-Final Office Action in U.S. Appl. No. 11/031,630.
Jun. 23, 2009 Notice of Allowance in U.S. Appl. No. 10/727,149 9 pgs.
Jul. 23, 2009 Notice of Allowance in U.S. Appl. No. 10/727,149 4 pgs.
Feb. 10, 2009 Amendment in U.S. Appl. No. 10/727,149 9 pgs.
Nov. 10, 2008 Office Action in U.S. Appl. No. 10/727,149 19 pgs.
Aug. 31, 2009 Amendment in U.S. Appl. No. 10/727,096 20 pgs.
Apr. 29, 2009 Office Action in U.S. Appl. No. 10/727,096 18 pgs.
Feb. 17, 2009 Amendment in U.S. Appl. No. 10/727,096 18 pgs.
Nov. 14, 2008 Office Action in U.S. Appl. No. 10/727,096 16 pgs.
Aug. 21, 2009 Office Action in U.S. Appl. No. 11/031,631 7 pgs.
Jun. 3, 2009 Amendment in U.S. Appl. No. 11/031,631 10 pgs.
Mar. 9, 2009 Supplemental Office Action in U.S. Appl. No. 11/031,631 7 pgs.
Feb. 24, 2009 Office Action in U.S. Appl. No. 11/031,631 8 pgs.
Jan. 16, 2009 Amendment in U.S. Appl. No. 11/031,631 14 pgs.
Sep. 3, 2009 Amendment in U.S. Appl. No. 11/031,630 7 pgs.
Jun. 11, 2009 Office Action in U.S. Appl. No. 11/031,630 5 pgs.
May 7, 2009 Amendment in U.S. Appl. No. 11/031,630 19 pgs.
Mar. 9, 2009 Office Action in U.S. Appl. No. 11/031,630 7 pgs.
Dec. 17, 2008 Amendment in U.S. Appl. No. 11/031,630 14 pgs.
Office Action dated Dec. 9, 2009 for U.S. Appl. No. 10/727,096, filed Dec. 2, 2003, Inventor: David K. Swanson (13 pages).
Notice of Allowance dated Feb. 12, 2008 for U.S. Appl. No. 10/784,316, filed Feb. 19, 2004, Inventor: David K. Swanson (1 page).
Amendment dated Dec. 21, 2009 for U.S. Appl. No. 11/031,631, filed Jan. 8, 2005; Inventor: David K. Swanson (11 pages).
Notice of Allowance dated Feb. 26, 2010 for U.S. Appl. No. 11/031,631, filed Jan. 8, 2005; Inventor: David K. Swanson (4 pages).
Office Action dated Nov. 20, 2009 for U.S. Appl. No. 11/067,391, filed Feb. 25, 2005; Inventor: Greg Eberl (8 pages).
Amendment dated Jan. 12, 2010 for U.S. Appl. No. 11/067,391, filed Feb. 25, 2005; Inventor Greg Eberl (8 pages).
Office Action dated Apr. 5, 2010 for U.S. Appl. No. 11/067,391, filed Feb. 25, 2005; Inventor Greg Eberl (8 pages).
Notice of Allowance dated Dec. 4, 2009 for U.S. Appl. No. 11/031,630, filed Jan. 8, 2005; Inventor: David K. Swanson (6 pages).
Notice of Allowance dated Apr. 8, 2010 for U.S. Appl. No. 11/031,630, filed Jan. 8, 2005; Inventor: David K. Swanson (4 pages).

* cited by examiner

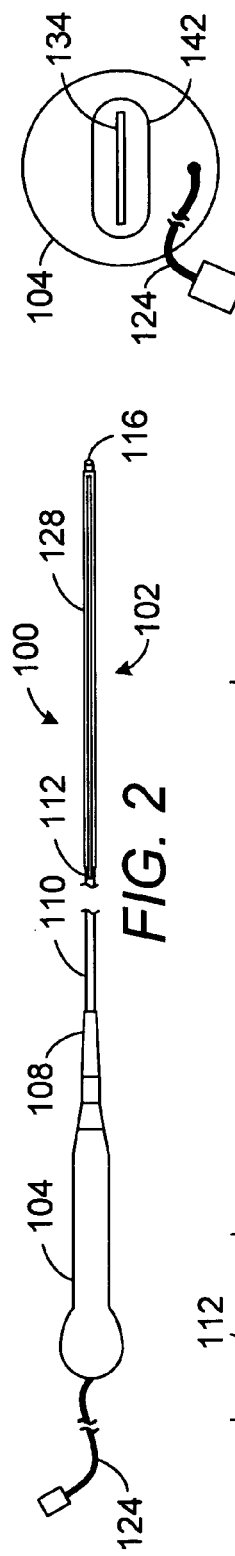
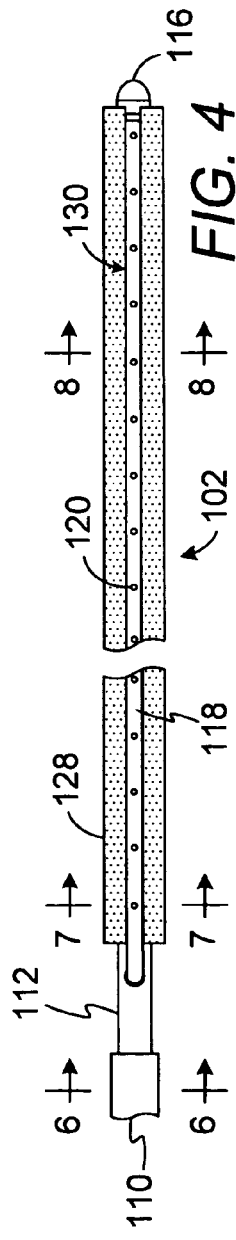
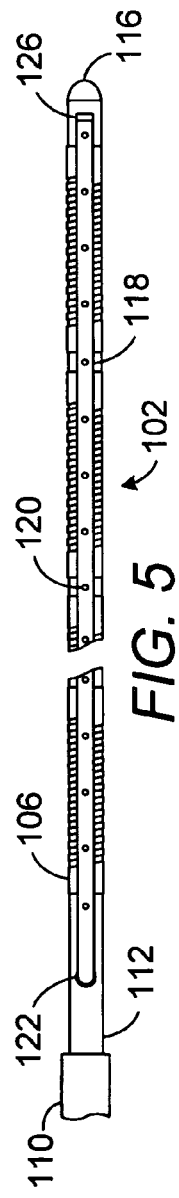
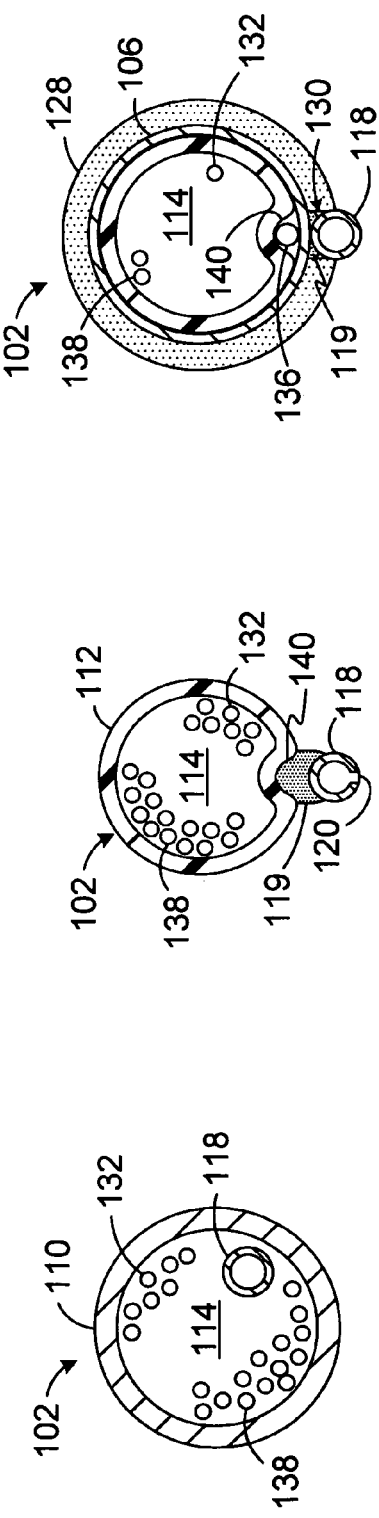

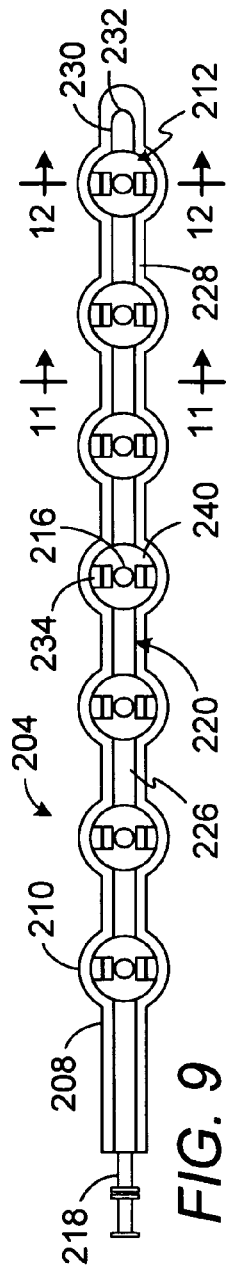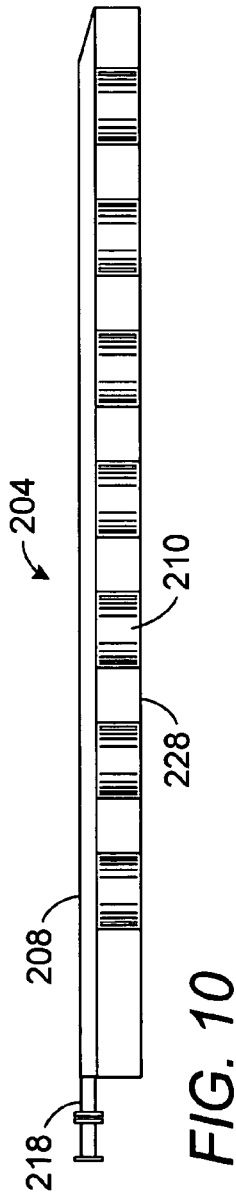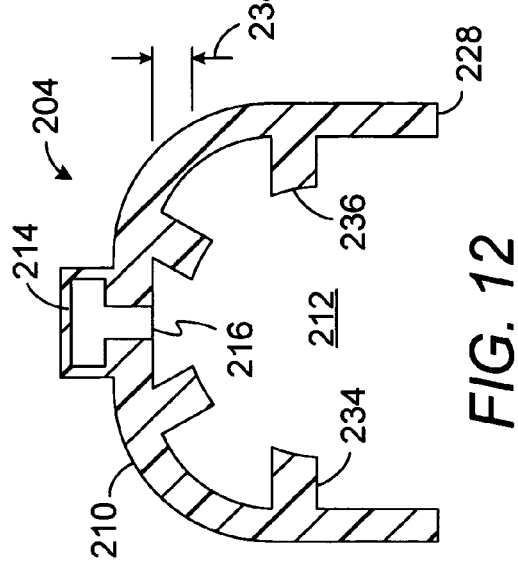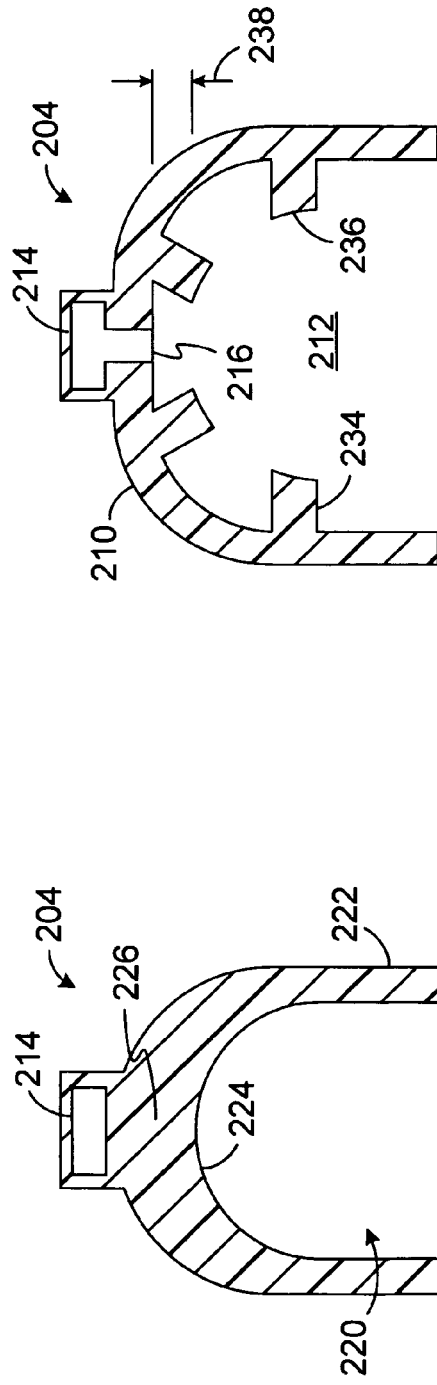
FIG. 9
FIG. 10
FIG. 11
FIG. 12

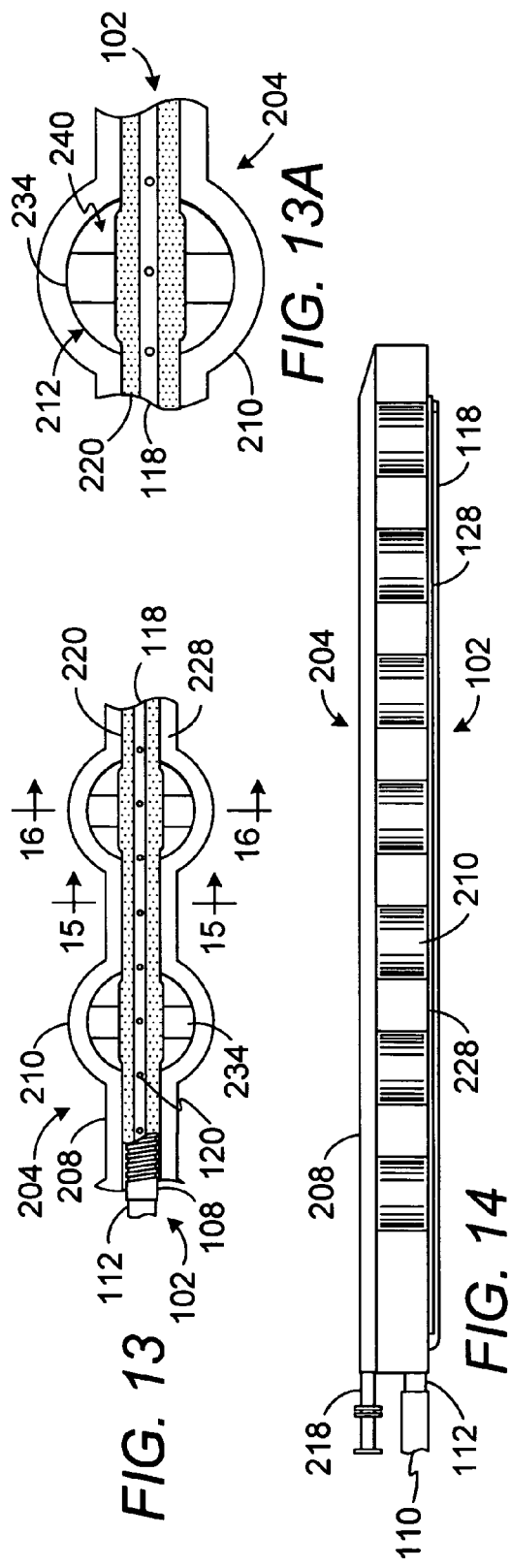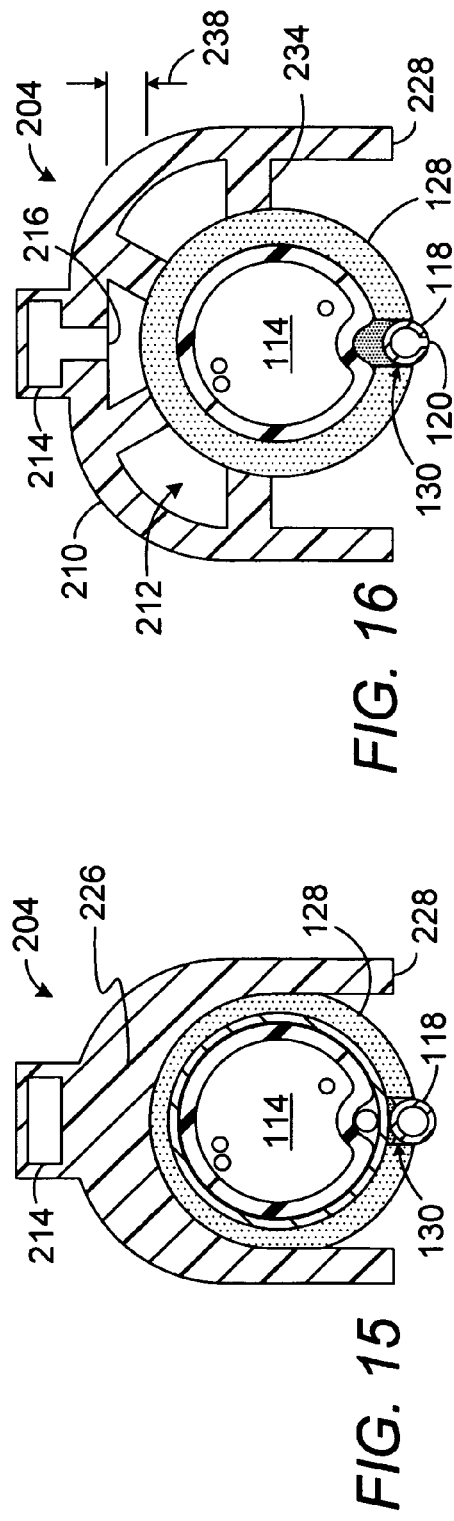

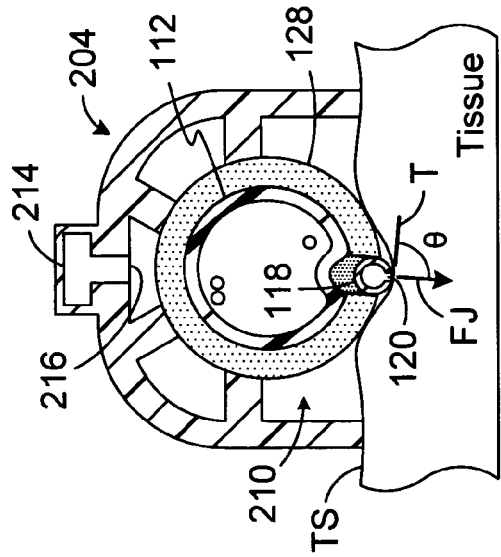
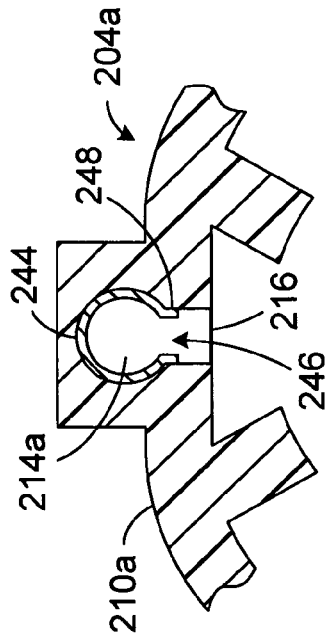
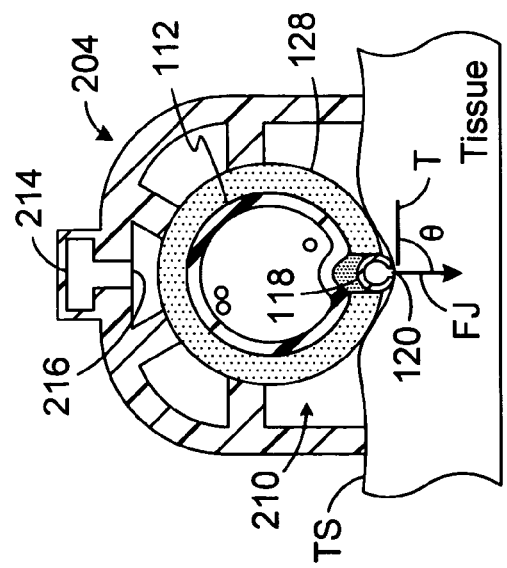
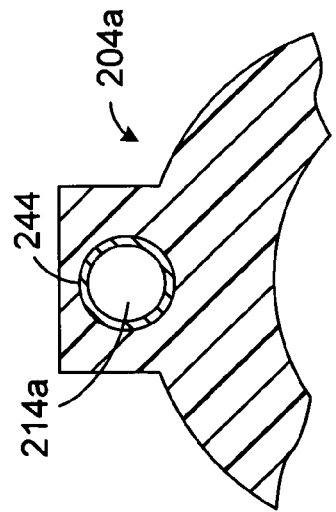

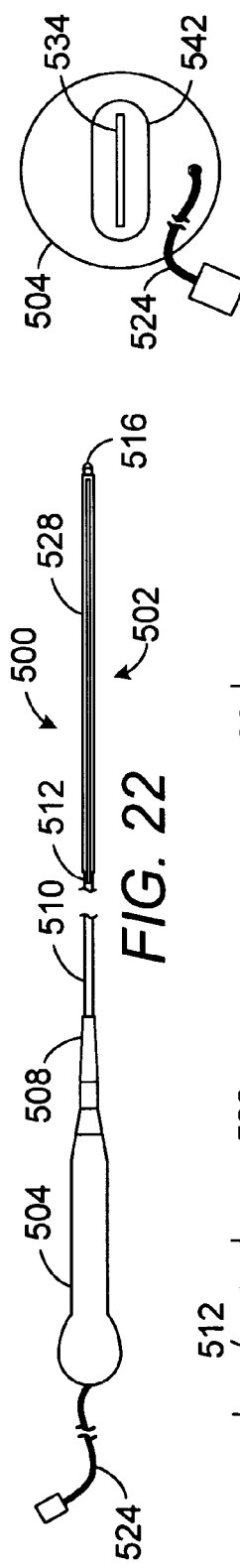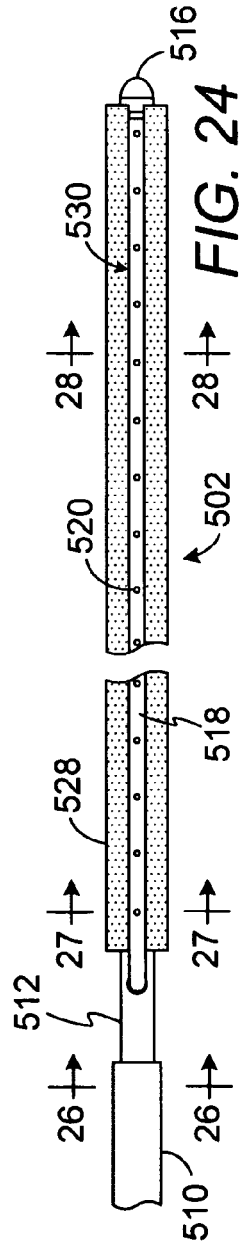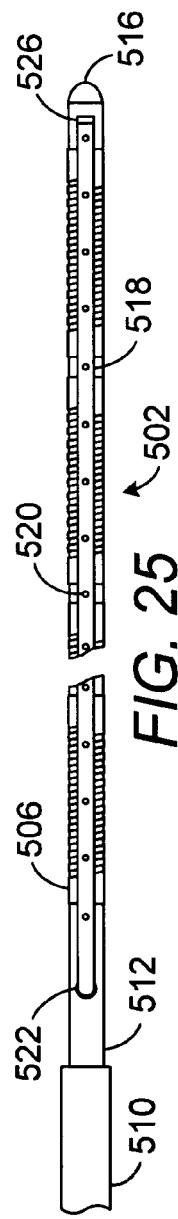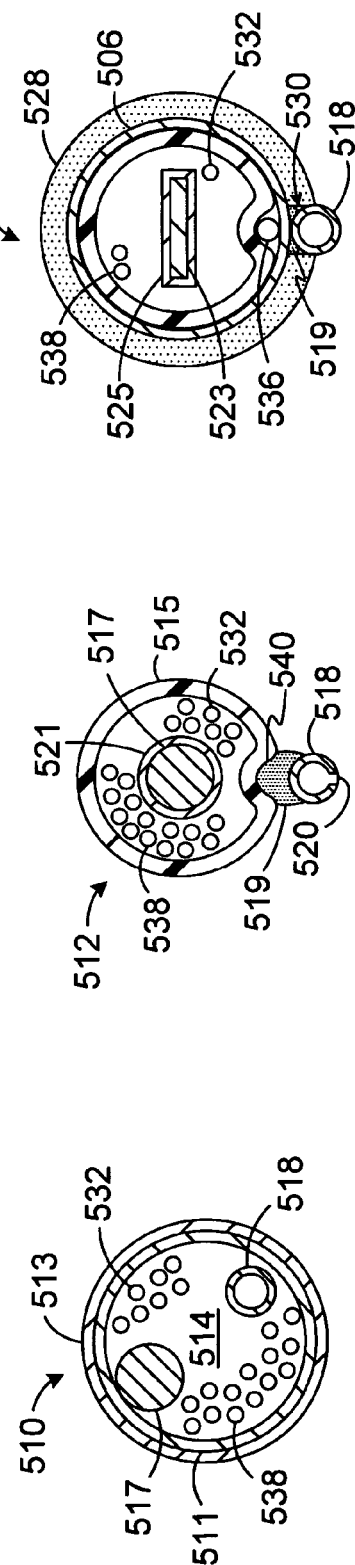

FLUID INJECTING DEVICES AND METHODS AND APPARATUS FOR MAINTAINING CONTACT BETWEEN FLUID INJECTING DEVICES AND TISSUE

BACKGROUND OF THE INVENTIONS

1. Field of Inventions

The present inventions relate generally to devices for performing diagnostic and therapeutic operations on body tissue.

2. Description of the Related Art

There are many instances where diagnostic and therapeutic elements must be positioned adjacent to body tissue. One instance involves the formation of therapeutic lesions to the treat cardiac conditions such as atrial fibrillation, atrial flutter and arrhythmia. Therapeutic lesions may also be used to treat conditions in other regions of the body including, but not limited to, the prostate, liver, brain, gall bladder, uterus and other solid organs. Typically, the lesions are formed by ablating tissue with one or more electrodes. Electromagnetic radio frequency ("RF") energy applied by the electrode heats, and eventually kills (i.e. "ablates"), the tissue to form a lesion. During the ablation of soft tissue (i.e. tissue other than blood, bone and connective tissue), tissue coagulation occurs and it is the coagulation that kills the tissue. Thus, references to the ablation of soft tissue are necessarily references to soft tissue coagulation. "Tissue coagulation" is the process of cross-linking proteins in tissue to cause the tissue to jell. In soft tissue, it is the fluid within the tissue cell membranes that jells to kill the cells, thereby killing the tissue. Depending on the procedure, a variety of different electrophysiology devices may be used to position a plurality of electrodes at the target location.

In recent years, devices such as surgical soft tissue coagulation probes (or "probes") that carry one or more diagnostic or therapeutic elements have been developed. These probes may be used, for example, in endocardial and epicardial procedures where access to the heart is obtained by way of a thoracostomy, thoracotomy or median sternotomy. Such probes also allow endocardial lesions to be formed as a secondary procedure during a primary open heart surgical procedure such as mitral valve replacement, aortic valve replacement, and coronary artery bypass grafting. In either case, it is frequently desirable to create continuous transmural linear lesions for therapeutic purposes.

One method of increasing the effectiveness of surgical probes involves the injection of conductive fluid into the target tissue before and/or during the tissue coagulation procedure. U.S. Pat. No. 6,814,731 discloses surgical probes that include jet injectors which inject conductive fluid into tissue as well as electrodes that transmit energy to tissue. The conductive fluid decreases the electrical resistance of the tissue in the vicinity of the electrodes. The decrease in electrical resistance shifts the hottest isothermal region deeper into the tissue, thereby enabling higher power to be delivered without causing char or excessive surface desiccation to occur. Higher power results in a larger volume of tissue being heated to a temperature sufficient to coagulate tissue (above 50° C.) and, therefore, a wider and deeper lesion. Lesion depth is important because lesions which are not transmural may fail to cure the patient's medical condition.

The present inventor has determined that devices which inject fluid into tissue are susceptible to improvement. For example, the present inventor has determined that there are instances where the orientation of the jet injectors relative to the target tissue is important and that it would be desirable to insure that the proper orientation of the jet injectors, as well as good jet injectors/tissue contact, is established and maintained.

SUMMARY OF THE INVENTIONS

A method of supply energy to tissue in accordance with a present invention includes the steps of securing an energy transmission device and a fluid injection device adjacent to the tissue with suction force, injecting conductive fluid into the tissue, and transmitting energy into the tissue. An apparatus in accordance with a present invention includes a suction device, an energy transmission device carried by the suction device and a fluid injection device associated with the suction device and the energy transmission device. There are a variety of advantages associated with such inventions. For example, the use of suction force causes the surface of the target tissue structure to be positioned tightly against the fluid injection device which, in turn, results in the tissue surface will being substantially perpendicular to the injection device (or within the critical angle). Such positioning allows fluid jets from the injection device to reliably penetrate tissue. The suction force may also be used to promote evaporative cooling during energy transmission, which result in wider and deeper lesions than would otherwise be produced.

A suction device for use with a probe that includes at least one energy transmission device and a wettable structure in accordance with a present invention includes a suction pod defining a suction region and including a suction aperture within the suction region, a connector configured to secure the probe to the suction device, and at least one support device configured to engage the wettable structure and maintain a predetermined space between the wettable structure and the suction aperture. There are a variety of advantages associated with such inventions. For example, the support device prevents the wettable structure from entering the suction aperture, which can be detrimental to the therapeutic operation.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of exemplary embodiments of the inventions will be made with reference to the accompanying drawings.

FIG. 2 is a plan view of a probe in accordance with one embodiment of a present invention.

FIG. 3 is an end view of the probe illustrated in FIG. 2.

FIG. 4 is a plan view of the distal portion of the probe illustrated in FIG. 2.

FIG. 5 is a plan view of the distal portion of the probe illustrated in FIG. 2 with the wettable structure removed.

FIG. 6 is a section view taken along line 6-6 in FIG. 4.

FIG. 7 is a section view taken along line 7-7 in FIG. 4.

FIG. 8 is a section view taken along line 8-8 in FIG. 4.

FIG. 9 is a bottom view of a suction device in accordance with one embodiment of a present invention.

FIG. 10 is a side view of the suction device illustrated in FIG. 9.

FIG. 11 is a section view taken along line 11-11 in FIG. 9.

FIG. 12 is a section view taken along line 12-12 in FIG. 9.

FIG. 13 is a bottom view of showing a portion of the probe illustrated in FIGS. 2-8 secured to the suction device illustrated in FIGS. 9-12.

FIG. 13A is an enlarged view of a portion of FIG. 13.

FIG. 14 is a side view of showing a portion of the probe illustrated in FIGS. 2-8 secured to the suction device illustrated in FIGS. 9-12.

FIG. 15 is a section view taken along line 15-15 in FIG. 13.

FIG. 16 is a section view taken along line 16-16 in FIG. 13.

FIG. 17 is a section view showing fluid being injected into tissue.

FIG. 18 is a section view showing fluid being injected into tissue.

FIG. 19 is a section view of a portion of a suction device in accordance with one embodiment of a present invention.

FIG. 20 is a section view of another portion of the suction device illustrated in FIG. 19.

FIG. 22 is a plan view of a surgical probe in accordance with one embodiment of a present invention.

FIG. 23 is an end view of the surgical probe illustrated in FIG. 22.

FIG. 24 is a plan view of the distal portion of the surgical probe illustrated in FIG. 22.

FIG. 25 is a plan view of the distal portion of the surgical probe illustrated in FIG. 22 with the wettable structure removed.

FIG. 26 is a section view taken along line 26-26 in FIG. 24.

FIG. 27 is a section view taken along line 27-27 in FIG. 24.

FIG. 28 is a section view taken along line 28-28 in FIG. 24.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:
 I. Exemplary System Overview
 II. Exemplary Probe For Use With Suction Systems
 III. Exemplary Power Supply and Control
 IV. Exemplary Fluid Supply
 V. Exemplary Suction System
 VI. Exemplary Methods
 VII. Exemplary Surgical Probe
The section titles and overall organization of the present detailed description are for the purpose of convenience only and are not intended to limit the present inventions.

This specification discloses a number of structures, mainly in the context of cardiac treatment, because the structures are well suited for use with myocardial tissue. Nevertheless, it should be appreciated that the structures are applicable for use in therapies involving other types of soft tissue. For example, various aspects of the present inventions have applications in procedures concerning other regions of the body such as the prostate, liver, brain, gall bladder, uterus and other solid organs.

I. Exemplary System Overview

Figure 1:
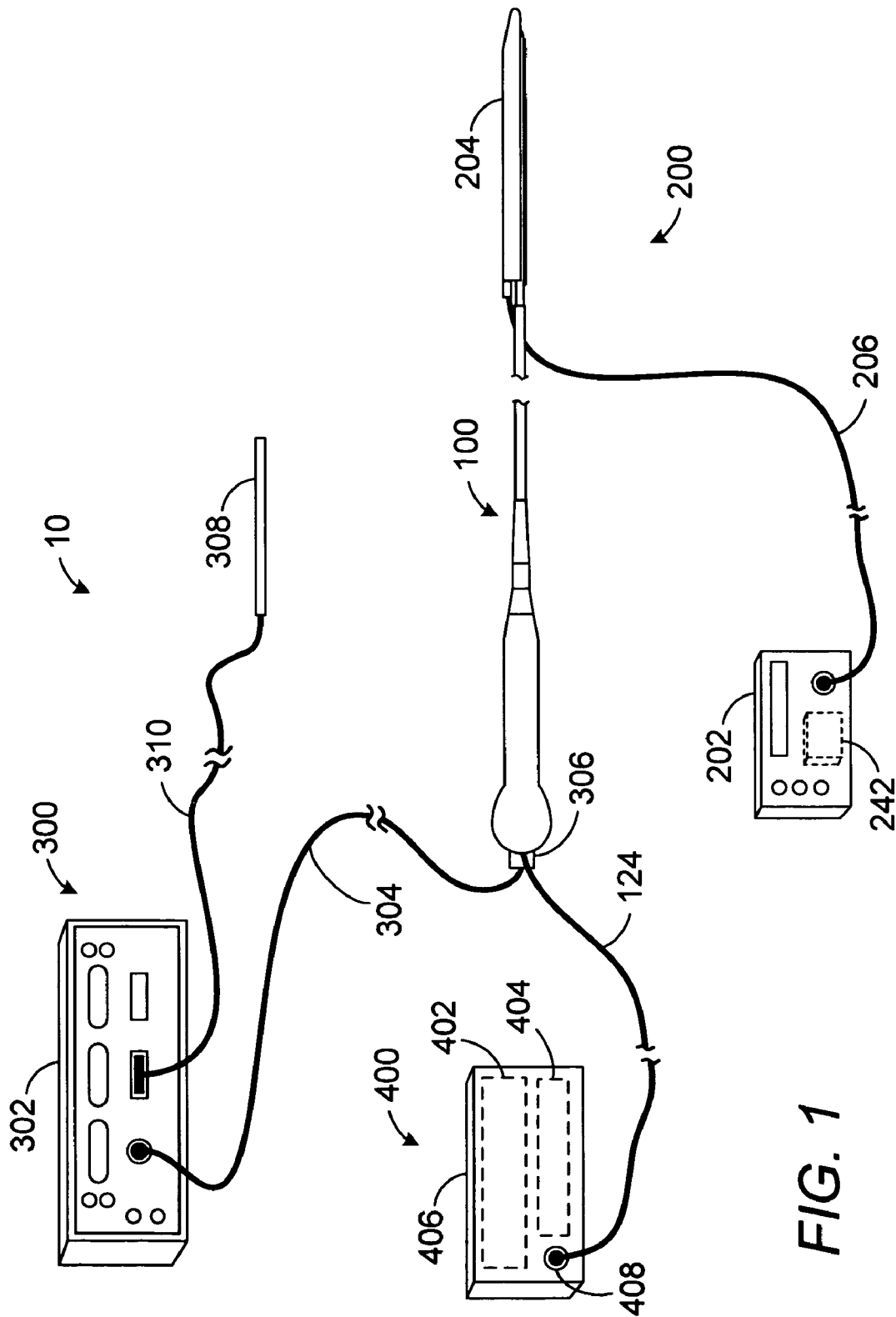
FIG. 1 is a perspective view of an electrophysiology system in accordance with one embodiment of a present invention.

As illustrated for example in FIG. 1, an electrosurgical system 10 in accordance with a preferred embodiment of a present invention consists of a probe 100 and a suction system 200. The exemplary probe 100 is cable of both supplying tissue coagulation energy to tissue and injecting conductive fluid into the tissue. The exemplary suction system 200 includes a suction source 202 and a suction device 204 that may be removably secured to the distal portion of the probe 100. When the suction source 202 is actuated, the suction device 204 will fix the position of the distal portion of the probe 100 relative to the target tissue and insure that there is good contact between the tissue and the energy transmitting portion of the probe. In addition, the suction device will insure that the conductive fluid leaves the probe 100 at the proper angle relative to the tissue surface (e.g. perpendicular to the tissue or within the critical angle). A power supply and control system 300 may be used to supply power to the probe 100 and a fluid supply device 400 may be used to supply pressurized conductive fluid to the fluid injecting portions of the probe. The fluid supply device 400 may also be used to supply fluid at lower, sub-injection pressures during the tissue coagulation process for evaporative cooling purposes.

II. Exemplary Probe For Use With Suction Systems

As illustrated for example in FIGS. 2-8, the probe 100 in the exemplary electrosurgical system 10 includes a shaft 102, a handle 104, and a plurality of electrodes 106 or other energy transmission elements on the shaft. A strain relief element 108 may also be provided. The exemplary shaft 102 includes a proximal portion 110 and a distal portion 112. The proximal portion 110, which is relatively long (e.g. about 30 cm to 100 cm for cardiac treatment applications) and flexible, is secured to the handle 104. This allows the proximal portion 110 to be conveniently draped over the patient and beyond after the distal portion 112 and electrodes 106 have been positioned at the target tissue location. The distal portion 112, which carries the electrodes 106, is relatively short (e.g. about 2 cm to 25 cm for cardiac treatment applications) and is also flexible. The shaft proximal and distal portions 110 and 112 may be a unitary structure or, alternatively, may be two separate structures (as shown) that are secured to one another during assembly. In either case, the shaft proximal and distal portions 110 and 112 each define an internal lumen 114. A tip member 116, which seals the lumen 114, is secured to the distal end of the shaft distal portion 112 with adhesive or other suitable instrumentalities.

The shaft proximal and distal portions 110 and 112 are preferably formed from a flexible, electrically non-conductive material such as biocompatible thermoplastic material (e.g. unbraided Pebax® material, polyethylene, or polyurethane). With respect to size, the outer diameter of the proximal portion 110 is about 3 mm to about 5 mm in the exemplary implementation, while the outer diameter of the distal portion 112 is about 1.66 mm to 3.3 mm. The exemplary material and dimensions may be adjusted as desired or if applications so require.

Although the present inventions are not limited to any particular number or size, the exemplary probe 100 includes seven (7) spaced electrodes 106. The spaced electrodes 106 are preferably in the form of wound, spiral closed coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. Preferred coil electrodes are disclosed in U.S. Pat. Nos. 5,797,905 and 6,245,068. With respect to size, the exemplary flexible electrodes 106 are about 4 mm to about 20 mm in length. In a preferred embodiment, the electrodes are 12.5 mm in length with 1 mm to 3 mm spacing, which will result in an energy transmission region that is about 1 cm to about 14 cm in length and the creation of continuous lesion patterns in tissue when coagulation energy is applied simultaneously to adjacent electrodes.

Alternatively, the electrodes 106 may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel, silver or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks. Open coil electrodes may also be employed.

The exemplary probe 100 illustrated in FIGS. 2-8 is also configured to inject conductive fluid into tissue. More specifically, the exemplary probe 100 includes a fluid tube 118 with a plurality of injection ports 120. The fluid tube 118 is secured, by adhesive 119 or other suitable instrumentalities, to the electrodes 106 in such a manner that the injection ports are aligned with the longitudinal (i.e. central) axis of the shaft distal portion and will direct fluid in the radial direction. The adhesive 119 may also be used to fill the space between the linear channel 140 (discussed below) and the fluid tube 118. The fluid tube 118 enters the shaft 102 through an aperture 122 (FIG. 5) located near the proximal end of the distal section 112. The fluid tube 118 extends to the handle 106, where it is connected to a connector tube 124. The connector tube 124 may be connected to the pressurized fluid supply device 400 (FIG. 1). The fluid tube 118 may, alternatively, simply extend along the exterior of the shaft before entering (or not entering) the handle 106. A cap 126 is secured to the distal end of the fluid tube 118. The distal end of the fluid tube 118 may, alternatively, be sealed with adhesive or other suitable instrumentalities.

Although the present inventions are not limited to any particular sizes, injection port spacing and materials, the fluid tube 118 in the exemplary embodiment has an internal diameter of about 2 French (0.66 mm). The fluid injection ports 120 in the illustrated embodiment are about 0.05 mm to about 0.20 mm in diameter with 5 mm spacing between adjacent injection ports. The size of the fluid tube 118, as well as the size and spacing of the fluid injection ports 120, may be increased or decreased to suit particular applications. Suitable materials for the fluid tube 118 include polyimide and malleable, fully annealed stainless steel, copper and silver.

The exemplary probe 100 is also provided with a porous, wettable structure 128 that is carried on the shaft distal portion 112. The wettable structure 128 is configured to retain conductive ionic fluid so that energy may be transmitted from the electrodes 106 to tissue by way of the conductive fluid. The wettable structure 128, which also cools tissue (primarily by vaporization of the conductive fluid) and prevents desiccation, receives the conductive fluid from the fluid tube 118. Suitable materials include foams, such as open cell foams, reticulated foams, non-reticulated foams, fine cell foams and hydrocolloide foams. Other suitable materials include hydrogels, thick woven biocompatible materials (e.g. Dacron®), cotton and cellulose. The electrical resistance of the wettable structure 128 may also be reduced by adding conductive fibers thereto (not shown) in the manner described in U.S. application Ser. No. 11/031,630, which is incorporated herein by reference.

The exemplary wettable structure 128, which expends slightly beyond the proximal-most and distal-most electrodes 106, is substantially cylindrical in shape and includes a slot 130 that is aligned with the fluid tube 118. In addition to absorbing the conductive fluid, the wettable structure 128 prevents the fluid tube 118 from digging too far into the tissue. In the illustrated embodiment, the thickness of the wettable structure 128 is about one-half of the diameter of the fluid tube 118, i.e. about 0.3 mm to 0.4 mm. Anchoring devices (not shown) may be positioned at the longitudinal ends of the wettable structure 128 to hold it in place if necessary.

III. Exemplary Power Supply and Control

As illustrated for example in FIGS. 2-8, the electrodes 106 in the exemplary probe 100 are electrically coupled to individual power wires 132 that conduct coagulating energy to them. The power wires 132 are passed in conventional fashion through the shaft lumen 114 to a connector 134 within the handle 104. Suitable connectors include PC boards, edge card connectors, subminiature D connectors, ribbon cable connectors, and pin and socket connectors. A plurality of temperature sensors 136 such as thermocouples or thermistors, may be located on, under, abutting the longitudinal end edges of, or in between, the electrodes 106. A reference thermocouple (not shown) may also be provided. In the exemplary implementation, temperature sensors 136 are located at both longitudinal ends of each electrode 106. The temperature sensors 136 are connected to the connector 134 by signal wires 138 that also pass though the shaft lumen 114.

In the exemplary embodiment, the temperature sensors 136 are preferably located within a linear channel 140 (FIGS. 7 and 8) that is formed in the shaft distal portion 112. The linear channel 140 insures that the temperature sensors 136 will all face in the same direction (e.g. facing tissue) and be arranged in linear fashion. This arrangement results in more accurate temperature readings which, in turn, results in better temperature control. As such, the actual tissue temperature will more accurately correspond to the temperature set by the physician on the power supply and control device, thereby providing the physician with better control of the lesion creation process and reducing the likelihood that embolic materials will be formed. Such a channel may be employed in conjunction with any of the electrode support structures disclosed herein.

It should be noted that, in those instances where it is anticipated that fluid will continue to be transmitted to the tissue surface by way of the fluid tube 118 for evaporative cooling purposes during the tissue coagulation process, it may be disable to configure the probe such that the fluid tube is moved 20° in one direction from the position illustrated in FIG. 8, and the temperature sensors 136 (and linear channel 140) are moved 20° in the other direction, in order to insure that the fluid does not interfere with temperature sensing.

The power supply and control system 300 in the exemplary implementation illustrated in FIG. 1 includes an electrosurgical unit ("ESU") 302 that supplies and controls power, such RF power. A suitable ESU is the Model 4810A ESU sold by Boston Scientific Corporation of Natick, Mass. The ESU 302 transmits energy to the electrodes 106 and receives signals from the temperature sensors 136 by way of a cable 304 and a connector 306. The connector 306 is configured to be inserted into a slot 142 (FIG. 3) on the probe handle 104 and to mate with the connector 134. The exemplary ESU 302 illustrated is operable in a bipolar mode, where tissue coagulation energy emitted by one of the electrodes 106 is returned through one of the other electrodes, and a unipolar mode, where the tissue coagulation energy emitted by the electrodes 106 is returned through one or more indifferent electrodes 308 that are externally attached to the skin of the patient with a patch, or one or more electrodes (not shown) that are positioned in the blood pool, and a cable 310. The exemplary ESU 302 is also configured to individually power and control each electrode 106. Suitable temperature sensors and RF power supply and control devices are disclosed in U.S. Pat. Nos. 5,456,682, 5,582,609 and 5,755,715. Another alternative is to supply power in the combined bi-polar/uni-polar mode described in U.S. Pat. Pub. No. 2004/0162556. In any case, the amount of power required to coagulate tissue ranges from 5 to 150 w and depends on parameters such as set temperature and the flow rate of the fluid.

IV. Exemplary Fluid Supply

As noted above, the exemplary probe 100 includes a fluid tube 118 with a plurality of fluid injection ports 120. Pressurized conductive fluid, which is supplied to the fluid injection ports 120 by way of the fluid tube 118, is injected into the tissue adjacent to the electrodes 106 immediately prior to (or concurrent with the initiation of) a tissue coagulation procedure. The conductive fluid decreases the electrical resistance of the tissue in the vicinity of the electrodes 106 and, accordingly, facilitates the formation of wider and deeper lesions. The conductive fluid may also continue to be supplied to the tissue surface for the duration of the tissue coagulation procedure at a lower, non-injection pressure by way of the fluid tube 118 and fluid injection ports 120. The conductive fluid supplied at the non-injection pressure will saturate the wettable structure 128, thereby establishing an electrically conductive path between the electrodes 106 and the tissue, and be vaporized, thereby cooling the electrodes and tissue surface. The evaporative cooling, which is discussed in Section V below, also facilitates the formation of wider and deeper lesions.

Turning to FIG. 1, the conductive fluid may be supplied under pressure to the fluid tube 118 on the probe 100 by the fluid supply device 400. The exemplary fluid supply device 400 includes a reservoir 402 and a pump 404 within a housing 406. As used herein, the term "pump" covers any device that supplies fluid at a pressure sufficient to result in jet injection. For example, the pump 404 may consist of a pneumatic gas ($CO_2$ or $NO_2$) canister and plunger arrangement of the type illustrated in U.S. Pat. No. 6,814,731, which is incorporated herein by reference. The pump 404 is connected to the reservoir 402 and to an outlet connector 408 which may, in turn, be connected to the connector tube 124. Alternatively, the reservoir and pump may be located within the probe handle 104 and connected directly to the fluid tube 118. In either case, the pump 404 creates a high pressure within the fluid tube 118 that ejects a fluid jet FJ, i.e. a narrow stream of conductive fluid, though the fluid injection ports 120 (note FIGS. 17 and 18).

The amount of pressure required in the fluid tube 118 depends on the desired penetration depth and the type of tissue being treated. Fatty tissue is, for example, relatively easy to penetrate and would require lower pressures than muscle tissue. As such, the pressure of the conductive fluid being delivered by the fluid supply device 400 may be adjusted by the fluid supply device, or by a device (not shown) between the fluid supply device and the fluid tube 118, using mechanical or electronic control techniques. In the exemplary context of epicardial lesion formation, the pressure within the fluid tube 118 at each injection port 120 should be within a range of about 500 psi to about 1500 psi. Such pressure cause the fluid jets FJ to leave the injection ports 120 at a sufficient speed to penetrate heart tissue to a depth within the range of about 2 mm to about 5 mm. The volume of conductive fluid through each injection port will typically be about 50 μl to about 100 μl (i.e. about 3 ml total) when an epicardial lesion is formed by the probe 100.

It should also be noted that because the fluid tube 118 has a small diameter, a substantial pressure drop occurs between the proximal end of the fluid tube and the distal portion of the fluid tube which, in the illustrated embodiment, is the portion of the fluid tube that is located outside the probe shaft 102 and includes the injection ports 120. The pressure at the proximal end of the fluid tube 118 needs to be high enough to produce the desired injection pressures at the injections ports 120 associated with the distal portion of the fluid tube, i.e. within a range of about 500 psi to about 1500 psi in the exemplary epicardial environment, despite the pressure drop. Accordingly, the pressure at the proximal end of the fluid tube 118 should be within a range of about 1000 psi to about 2000 psi in order to account for the pressure drop.

With respect to the conductive fluid itself, suitable conductive fluids include 10% saline (by weight), and in those instance where the required volume of conductive fluid is relatively small, potassium chloride (KCl) in a concentration of 2 mEq/ml may be used. Other suitable conductive fluids are discussed in U.S. Pat. No. 6,814,731.

V. Exemplary Suction System As illustrated for example in FIG. 1, and as noted above, the exemplary suction system 200 includes the suction source 202 and the suction device 204. The suction source 202 may be any suitable device that is capable of supplying the desired partial vacuum, which will typically range from about 100 mmHg to about 600 mmHg. The suction device 204, which is connected to the suction source 202 with a flexible suction tube 206, may be removably secured to the distal portion 112 of the probe 100. When the suction source 202 is actuated, the suction device 204 will affix itself to a tissue surface and hold the probe distal portion 112, including the electrodes 106 and fluid tube 118, in place relative to the tissue surface.

Turning to FIGS. 9-12, the exemplary suction device 204 includes a main body 208 and a plurality of individual suction pods 210. Each suction pod 210 defines a suction region 212. A suction line 214 extends through the main body 208 and is connected to each of the suction pods 210 by suction apertures 216. The suction tube 206 may be connected to the internal suction line 214 by a connector 218 such as, for example, the illustrated Luer connector. The suction device 204 also includes a connector that enables it to be removably secured to the probe distal portion 112 such that a portion of the probe is at least partially within a suction region 212. Although the present inventions are not limited to any particular connector, the connector in the exemplary embodiment is a slot 220 into which the probe distal portion 112 may be inserted. The slot 220 is defined by the portions of the main body 208 that are located proximal of the proximal-most suction pod 210, between the suction pods, and distal of the distal-most suction pod.

The exemplary slot 220 is generally U-shaped in cross-section. The distance between the linear portions 222, as well as the diameter of the semi-circular portion 224, will preferably be slightly less than the diameter of the probe distal portion 112 (including the wettable structure 128). As such, the probe distal portion 112 may be removably pressed into the slot 220 to create an air-tight interference fit therebetween. Additionally, the main body includes suction pod separators 226 that define the top, semi-circular portion 224 of the slot 220. The separators 226 form an air-tight seal in the area between the suction pods 210 when the probe distal portion 112 is pressed against the semi-circular portion 224, thereby isolating the suction pods 210 from one another.

Another exemplary connector that may be employed is a slot that is generally C-shaped in cross-section. Such a connector would form a snap-fit connection with the associated probe.

When the exemplary suction device 204 is connected to the probe distal portion 112 by inserting the distal portion into the slot 220 in the manner illustrated in FIGS. 13-16, the bottom of the probe distal portion 112 and electrodes 106 will extend a short distance (e.g. about 0.5 mm) beyond the bottom surface 228 of the suction device. During use, the probe/suction device assembly will be pressed against tissue until the bottom surface 228 comes in contact with the tissue. The bottom surface 228 will form a seal with the tissue surface and air within the suction pods 210 will be drawn through the apertures 216 when the suction force is applied, thereby causing the suction device 204 to adhere to the tissue surface.

Turning to FIG. 17, the tissue surface TS will deflect and be pulled tightly against the fluid tube 118 when the suction force is applied. The tissue surface TS adjacent to the injection ports 120 will, therefore, be normal to the injection ports. In other words, the fluid jet FJ will be delivered to the tissue in a direction that defines an angle θ of 90° with the tangent T of the tissue surface TS at the injection port 120 if the tissue surface is curved after the application of suction force (as shown) or with the tissue surface itself if the tissue surface remains essentially flat and the suction device 204 deflects. This aspect of the invention is especially useful because the fluid jet FJ may not penetrate the tissue surface TS if it is not perpendicular to the tissue surface or within a "critical angle" therefrom. The critical angle, which is a function of diameter of the fluid jet FJ, the pressure within the fluid tube 118, and the velocity of the fluid jet, is 90° ± about 0° to 10° in the illustrated embodiment (i.e. θ=about 80° to about 100°). It should also be noted that, as illustrated in FIG. 18, the injection ports 120 (and fluid jets FJ) will be normal to the tissue surface TS even in those instance where the injection ports are not directly facing the tissue structure. This is because the suction force pulls the tissue surface TS against the fluid tube 118.

Another benefit associated with the present combination of suction and fluid injection is associated with the aforementioned fact that the suction insures that the tissue surface TS will be pulled tightly against the injection ports 120 during the fluid injection process. As a result, more consistent fluid injection may be realized at lower pressures than would be the case if there was space even a small space (e.g. 0.1 mm) between the injection ports 120 and the tissue surface TS.

It should also be noted that the probes and suction devices may be respectively configured in the exemplary implementation such that the size and spacing of the electrodes 106 corresponds to the size and spacing of the suction pods 210. For example, the probe 100 and suction device 204 are respectively configured such that the gaps between the electrodes 106 will be aligned with the center of the suction pods 210 when the distal portion 112 is secured to the suction device in the manner illustrated in FIGS. 13-16. More specifically, the distal portion 230 of the slot 220 and the probe distal portion 112 are configured such that, when tip member 116 is against the distal end 232 of the slot 220, gaps between the electrodes 106 will be aligned with the center of the suction pods 210, and the electrodes will be aligned with the portions of the slot between the suction pods.

Suction devices in accordance with the present inventions may also include apparatus that performs the function of preventing the portions of the wettable structure 128 from being sucked into the suction pod apertures 216, which would result in clogging of the suction line 214. For example, suction devices may include one or more supports within each of the suction pods. Referring to FIGS. 9, 12, 15 and 16, the exemplary suction device 204 includes four (4) struts 234 that extend into the suction region 212 of each suction pod 210. There are two (2) struts 234 on each side of the suction aperture 216 and the exemplary struts include curved contact surfaces 236 that are shaped so as to correspond to the shape of the probe. Additionally, the width of the struts is approximately the same as the diameter of the suction apertures 216.

So configured and positioned within the suction regions 212, the struts 234 create a first gap 238 (FIGS. 12 and 16) between the probe and the suction apertures 216 and second gaps 240 between the struts and the inner surfaces of the suction pods 210. The gaps 238 and 240 allow the suction process to proceed unimpeded, while the struts 234 will prevent portions of the wettable structure 128 from being sucked into the suction apertures 216.

The exemplary probe 100 and suction device 204 are configured such that may of the injection ports will be located within a respective suction pod 210 and conductive fluid may be supplied during the coagulation procedure at a low, non-injection pressure. In addition to providing fluid for the wettable structure 128, this arrangement allows coagulation procedures to proceed in such a manner that vaporization of the conductive fluid is the primary source of electrode cooling. This may be accomplished by applying a relatively high vacuum pressure to the suction device 204 generally. More specifically, in order to reduce the boiling point of the cooling fluid to the approximately 60° C. coagulation temperature, the absolute pressure within the suction pods 210 should be reduced to about 175 mm Hg. At sea level, an applied vacuum pressure of about −600 mm Hg will achieve 175 mm Hg within the suction pods 210. The vapor, which will be drawn into the suction device 202 by way of the suction line 214 and suction tube 206, will condense in the fluid receptacle 242 because it will be below the boiling temperature.

The specific size and shape of the suction device 204 will, of course, depend on the intended application, as will the choice of materials. Although the present inventions are not limited to any particular sizes, shapes or materials, one exemplary implementation that is especially well suited for cardiac treatment and use with the above-described probe 100 is described hereafter. The suction device 204 is formed, preferably by molding, from a soft, flexible biocompatible material such as silicone rubber or urethane that is capable of withstanding temperatures up to 120° C. without melting or burning. When molded, the suction device 204 will be an integrally formed (i.e. one piece) structure, although some or all of the connector 216 may be added after molding depending on the type of connector employed. The overall length of the suction device 204, not including the connector 216, will be slightly longer than the shaft distal portion 112, e.g. about 10 cm in an exemplary implementation where the distal portion is about 9 cm. The exemplary suction ports 210 are generally circular in shape when viewed from the bottom (FIG. 9) and have a diameter of about 11 mm and a depth of about 5 mm (FIG. 12). The distance between the top of the slot 220 and the bottom surface 228 is about 2.5 mm (FIG. 10). The suction apertures 216 are about 0.5 mm in diameter. The gap 238 will typically be about 0.5 mm to about 2.0 mm.

Suction devices in accordance with the present inventions may also be malleable. As illustrated in FIGS. 19 and 20, the suction line 214a in the exemplary suction device 204a, which is otherwise identical to the suction device 204, is formed by a malleable hypotube 244. The malleable hypotube 244 is connected to the connector 218, and includes apertures 246 that are aligned with the suction apertures 216. Preferably, such a suction device will be formed by an insert molding process. In order to prevent the hypotube apertures 246 from moving out of alignment with the suction apertures 216 during use, the malleable hypotube 244 is provided with cylindrical extensions 248 that are aligned with the hypotube apertures 246 and extend into the suction apertures 216.

VI. Exemplary Methods

Figure 21:
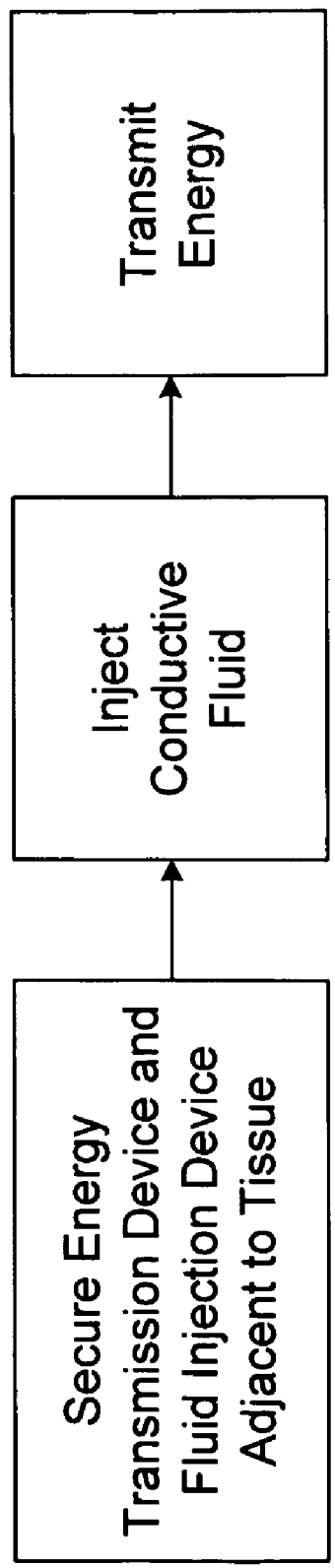
FIG. 21 is a flow chart showing a method in accordance with a present invention.

Referring to FIG. 21, the exemplary methods described above may be summarized as follows. A fluid injection device and an energy transmission device are secured to a body structure adjacent to a tissue surface, conductive fluid is injected below the tissue surface, and energy is transmitted to the tissue to form a lesion. The injection step may be initiated just prior to the initiation of the transmission step, simultaneously with the initiation of the transmission step, or just after the initiation of the transmission step. Suction may be used to secure the fluid injection device and an energy transmission device adjacent to the tissue surface and/or fluid may be delivered to the tissue surface for evaporative cooling purposes after the injection step. Although the present inventions are not limited to any particular therapeutic procedures, one exemplary application of the present methods is the formation of lesions associated with the epicardial treatment of atrial fibrillation.

VII. Exemplary Surgical Probe

The surgical probe 500 illustrated in FIGS. 22-28 is another example of a device that may include a fluid tube (and injection ports) on the exterior of the probe distal portion. The surgical probe 500 is similar in many respects to the probe 100 and similar elements are represented by similar reference numerals. The primary difference is associated with the fact that the probe 100 includes a shaft that is relatively long and flexible, while the shaft of the surgical probe 500 is relatively short and stiff. As such, the surgical probe may be used in procedures that do not employ suction as well as those that do. In those procedures that do not employ suction, the physician will manually force the distal portion of the surgical probe (including the electrodes and fluid injection ports) into contact with the tissue.

The surgical probe 500 includes a relatively short shaft 502, a handle 504, and a plurality of electrodes 506 or other energy transmission elements. The exemplary shaft 502 includes a proximal portion 510 and a distal portion 512. The shaft proximal portion 510 consists of a hypotube 511, which is either rigid or relatively stiff, and an outer polymer tubing 513 over the hypotube. The shaft proximal portion 510 may be from 4 inches to 18 inches (about 10 cm to about 46 cm) in length and is preferably 6 inches to 8 inches (about 15 cm to 20 cm). The shaft distal portion 512, which is preferably either malleable, somewhat flexible or some combination thereof, may be from 1 inch to 20 inches (about 2 cm to 50 cm) in length and is preferably 3 to 5 inches (about 7 cm to 13 cm).

As used herein the phrase "relatively stiff" means that the shaft (or distal section or other structural element) is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial. Rigid and somewhat flexible shafts are preferably formed from stainless steel, while malleable shafts are formed from annealed stainless steel.

In those instances where a malleable shaft proximal portion 512 is desired, the hypotube 511 may be a heat treated malleable hypotube. By selectively heat treating certain portions of the hypotube, one section of the hypotube can be made more malleable than the other. The outer tubing 513 may be formed from Pebax® material, polyurethane, or other suitable materials. Additional information concerning "relatively stiff" shafts is provided in U.S. Pat. No. 6,142,994, which is incorporated herein by reference.

As noted above, the shaft distal portion 512 can be either somewhat flexible, in that it will conform to a surface against which it is pressed and then spring back to its original shape when removed from the surface, malleable, or some combination thereof. In the exemplary implementation illustrated in FIGS. 22-28, the distal portion 512 includes a malleable proximal section and a flexible distal section. Although the relative lengths of the sections may vary to suit particular applications, the malleable proximal section and a flexible distal section are equal in length in the illustrated embodiment. The exemplary shaft distal portion 512 includes an outer member 515 that carries the electrodes 506. The outer member 515 is a flexible tubular structure which has an outer diameter that is, depending on the diameter of the electrodes 506, typically between about 2 mm and about 4 mm. The outer member 515 in the illustrated embodiment, which is intended for use in cardiovascular applications, typically has an outer diameter of about 3 mm. Suitable support structure materials include, for example, flexible biocompatible thermoplastic tubing such as unbraided Pebax® material, polyethylene, or polyurethane tubing.

Turning to the interior of the shaft distal portion 512, the exemplary malleable section includes a mandrel 517 (FIG. 27) made of a suitably malleable material, such as annealed stainless steel or beryllium copper, that may be fixed directly within the distal end of the shaft's hypotube 511 and secured by, for example, soldering, spot welding or adhesives. An insulating sleeve 521, which is preferably formed from Pebax® material, polyurethane, or other suitable materials, is placed over the mandrel 517. With respect to the flexible section, a spring member 523, which is preferably either a solid flat wire spring (FIG. 28), a round wire, or a three leaf flat wire Nitinol® spring, is connected to the distal end of the mandrel 517 with a crimp tube or other suitable instrumentality. The distal end of the spring member 523 is connected to the tip member 516 by, for example, an adhesive or welding. The tip member 516 is also secured to the distal end of the outer member 515. Other spring members, formed from materials such as 17-7 or carpenter's steel, may also be used. The spring member 523 is also enclosed within the insulating sleeve 525. The spring member 523 may be pre-stressed so that the distal tip is pre-bent into a desired shape. Additional details concerning distal sections that have a malleable proximal section and a flexible distal section are provided in U.S. Pat. No. 6,464,700, which is incorporated herein by reference.

The electrodes 506, including their size and spacing, are identical to the electrodes 106 and are electrically coupled to individual power wires 532 that conduct coagulating energy to them. The power wires 532 are passed in conventional fashion through the shaft lumen 514 to a connector 534 within the handle 504. Suitable connectors include PC boards, edge card connectors, subminiature D connectors, ribbon cable connectors, and pin and socket connectors. A plurality of temperature sensors 536 such as thermocouples or thermistors, may be located on, under, abutting the longitudinal end edges of, or in between, the electrodes 506. A reference thermocouple (not shown) may also be provided. In the exemplary implementation, temperature sensors 536 are located at both longitudinal ends of each electrode 506. The temperature sensors 536 are connected to the connector 534 by signal wires 538 that also pass though the shaft lumen 514. The temperature sensors 536 are also preferably located within a linear channel 540 (FIGS. 27 and 28) that is formed in the shaft distal portion 512. The power supply and control system 300 may be connected to the surgical probe 500 by way of a slot 542 (FIG. 23) on the surgical probe handle 504, and operated, in the manner described in Section III above.

The exemplary surgical probe 500 also includes a fluid tube 518 with a plurality of injection ports 520. The fluid tube 518 is secured, by adhesive 519 or other suitable instrumentalities, to the electrodes 506 in such a manner that the injection ports are aligned with the longitudinal (i.e. central) axis of the shaft distal portion and will direct fluid in the radial direction. The adhesive 519 may also be used to fill the space between the linear channel 540 and the fluid tube 518. The fluid tube 518 enters the shaft 502 through an aperture 522 (FIG. 25) located near the proximal end of the distal portion 512. The fluid tube 518 extends to the handle 506, where it is connected to a connector tube 524. The connector tube 524 may be connected to the pressurized fluid supply device 400 (FIG. 1). The fluid tube 518 may, alternatively, simply extend along the exterior of the shaft before entering (or not entering) the handle 506. A cap 526 is secured to the distal end of the fluid tube 518. The distal end of the fluid tube 518 may, alternatively, be sealed with adhesive or other suitable instrumentalities.

The exemplary surgical probe 500 is also provided with a porous, wettable structure 528 that is carried on the shaft distal portion 512. The exemplary wettable structure 528, which expends slightly beyond the proximal-most and distal-most electrodes 506, is substantially cylindrical in shape and includes a slot 530 that is aligned with the fluid tube 518.

With respect to materials, dimensions and operation, including operation in conjunction with the suction system 200 and the fluid supply device 400, the fluid tube 518, injection ports 520 and wettable structure 528 are essentially identical to the fluid tube, injection ports and wettable structure described above.

It is intended that the scope of the present inventions extend to all such modifications and/or additions and that the scope of the present inventions is limited solely by the claims set forth below. The inventions includes any combination of the elements from the various species and embodiments disclosed in the specification that are not already described as well as systems that comprise a power supply device (such as an ESU) and/or a fluid supply device in combination with any of the apparatus claimed below. Additionally, the scope of the inventions includes any combination of the elements from the various species and embodiments disclosed in the specification that are not already described.

I claim:

1. A suction device configured for use with a probe, the probe including a shaft having a proximal portion and a distal portion that carries at least one energy transmission device and a wettable structure around at least a portion of the energy transmission device, the suction device comprising:
    a main body defining a suction line;
    at least one suction pod defining a suction region and including a suction aperture in communication with the suction region and the suction line;
    a connector comprising a slot that is in-line with at least a portion of the suction region, the slot being configured to receive and secure the probe shaft to the suction device such that when the probe shaft is positioned within the connector, the probe shaft extends across the at least one suction pod and at least a portion of the wettable structure is within the suction region in spaced relation to the suction aperture; and
    at least one support device that extends from an inner surface of the at least one suction pod and into the suction region, the at least one support device being configured to engage the wettable structure and maintain a predetermined space between the wettable structure and the inner surface and between the wettable structure and the suction aperture.

2. The suction device as claimed in claim 1, wherein the at least one suction pod comprises a plurality of suction pods defining respective suction regions and the at least one support device comprises a plurality of support devices respectively positioned within the plurality of suction pods.

3. The suction device as claimed in claim 1, wherein the at least one support device comprises a plurality of struts that extend inwardly from the inner surface.

4. The suction device as claimed in claim 1, wherein the at least one suction pod comprises a flexible suction pod.

5. A suction device configured for use with a probe, the probe including a shaft having a proximal portion and a distal portion that carries at least one energy transmission device and a wettable structure around at least a portion of the energy transmission device, the suction device comprising:
    a main body defining a suction line
    at least one suction pod defining a suction region and including a suction aperture in communication with the suction region and the suction line;
    a connector comprising a slot that is in-line with at least a portion of the suction region, the slot being configured to receive and secure the probe shaft to the suction device such that when the probe shaft is positioned within the connector, the probe shaft extends across the at least one suction pod and at least a portion of the wettable structure is within the suction region in spaced relation to the suction aperture; and
    means for preventing the portion of the wettable structure from being pulled to the suction aperture by a suction force applied through the suction aperture.

6. The suction device as claimed in claim 5, wherein the at least one suction pod comprises a plurality of suction pods.

7. The suction device as claimed in claim 5, wherein the at least one suction pod comprises a flexible suction pod.

8. The suction device as claimed in claim 1, wherein the at least one support device comprises a plurality of support devices that extend inwardly from the inner surface of the at least one suction pod.

9. The suction device as claimed in claim 8, wherein at least one support device has a curved surface configured for contacting an outer surface of the probe shaft.

10. The suction device as claimed in claim 1, wherein the number of support devices on each side of the suction aperture is the same.

11. The suction device as claimed in claim 1, wherein the predetermined space between the wettable structure and the suction aperture is about 0.5 mm to about 2.0 mm.

12. The suction device as claimed in claim 1, wherein the at least one support device is configured to prevent the wettable structure from being sucked into the suction aperture.

13. The suction device as claimed in claim 1, wherein the suction aperture is in communication with and positioned above the connector.

14. The suction device as claimed in claim 13, wherein the suction aperture is positioned above the connector and above the suction region.

15. The suction device as claimed in claim 1, comprising a plurality of suction pods, the connector extending between at least two adjacent suction pods such that when the probe shaft is positioned with in the connector, the probe shaft extends across the plurality of suction pods.

16. The suction device as claimed in claim 15, the connector being defined by portions of the main body that are located proximal of a proximal-most suction pod of the plurality of suction pods and distal of the distal-most suction pod of the plurality of suction pods.

17. The suction device as claimed in claim 1, the main body comprising a top portion defining the suction line, and a bottom surface for contacting tissue such that when the probe shaft is positioned within the connector, a bottom of the probe shaft and the bottom surface of the main body contact tissue.

18. The suction device of as claimed in claim 1, the connector being configured such that the connector and the probe shaft are coaxially arranged when the probe shaft is inserted into the connector, and the probe shaft extends through the suction region.

19. A suction device configured for use with a probe, the probe including a shaft having a proximal portion and a distal portion that carries at least one energy transmission device and a wettable structure around at least a portion of the energy transmission device, the suction device comprising:

a main body defining a suction line;

a plurality of suction pods defining respective inner surfaces and bottom surfaces, the bottom surfaces being configured for contacting tissue, the plurality of suction pods defining respective suction regions extending between the respective inner and bottom surfaces and including respective suction apertures in fluid communication between respective suction regions and the suction line;

a connector defined by portions of the main body and extending between the plurality of suction pods, the connector comprising a slot defined by portions of the main body and being configured to receive and secure the probe shaft to the suction device such that when the probe shaft is positioned within the connector, the probe shaft extends across the plurality of suction pods and at least a portion of the wettable structure is within the suction region in spaced relation to the suction aperture; and at least one support device that extends from respective inner surfaces and into respective suction regions but not beyond the bottom surface such that the at least one support device engages the wettable structure and maintains a predetermined separation between the wettable structure and the inner surface and between the wettable structure and the suction aperture.

* * * * *